US009396835B2

(12) United States Patent
Kato et al.

(10) Patent No.: US 9,396,835 B2
(45) Date of Patent: Jul. 19, 2016

(54) METHOD FOR SUPPRESSING COPPER SULFIDE GENERATION IN OIL-FILLED ELECTRICAL EQUIPMENT

(75) Inventors: Fukutaro Kato, Chiyoda-ku (JP); Eiichi Nagao, Chiyoda-ku (JP); Tsuyoshi Amimoto, Chiyoda-ku (JP); Satoru Toyama, Chiyoda-ku (JP); Kota Mizuno, Chiyoda-ku (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 166 days.

(21) Appl. No.: 14/349,360

(22) PCT Filed: Nov. 30, 2011

(86) PCT No.: PCT/JP2011/077609
§ 371 (c)(1),
(2), (4) Date: Apr. 3, 2014

(87) PCT Pub. No.: WO2013/080315
PCT Pub. Date: Jun. 6, 2013

(65) Prior Publication Data
US 2014/0231726 A1    Aug. 21, 2014

(51) Int. Cl.
*G01N 33/28* (2006.01)
*H01B 3/20* (2006.01)
*H01F 27/12* (2006.01)

(52) U.S. Cl.
CPC .............. *H01B 3/20* (2013.01); *G01N 33/2858* (2013.01); *G01N 33/2835* (2013.01); *H01F 27/12* (2013.01); *Y10T 436/12* (2015.01); *Y10T 436/18* (2015.01)

(58) Field of Classification Search
CPC ....... G01N 33/20; G01N 33/26; G01N 33/28; G01N 33/2835; G01N 33/2858; G01N 33/287; H01B 3/20; H01F 27/12; Y10T 436/12; Y10T 436/18; Y10T 436/182
USPC .......... 436/55, 60, 73, 80, 119, 120; 252/574, 252/575
See application file for complete search history.

(56) References Cited

U.S. PATENT DOCUMENTS

| 8,728,565 | B2 * | 5/2014 | Kato ........................ | H01B 3/20 427/58 |
|---|---|---|---|---|
| 2010/0192673 | A1 | 8/2010 | Toyama et al. | |
| 2012/0197559 | A1 * | 8/2012 | Nagao .................. | G01N 33/287 702/58 |
| 2013/0034909 | A1 * | 2/2013 | Toyama ............... | G01N 33/287 436/80 |

FOREIGN PATENT DOCUMENTS

| CN | 101809688 A | 8/2010 |
|---|---|---|
| JP | 6-76635 A | 3/1994 |
| JP | 10-64336 A | 3/1998 |
| JP | 2010-027634 A | 2/2010 |
| JP | 2010-192823 A | 9/2010 |
| JP | 2011-171413 A | 9/2011 |

OTHER PUBLICATIONS

International Search Report (PCT/ISA/210) mailed on Feb. 14, 2012, by the Japanese Patent Office as the International Searching Authority for International Application No. PCT/JP2011/077609.
Notice of Grounds of Rejection mailed Aug. 21, 2012 for Japanese Application No. 2012-525562.
Decision to Grant Patent mailed Jan. 8, 2013 for Japanese Application No. 2012-525562.
CIGRE WG A2-32, Copper sulphide in transformer insulation, Final Report Brochure 378, 2009, pp. 1-35.
F. Scatiggio et al., Corrosive Sulfur in Insulating Oils: Its Detection and Correlated Power Apparatus Failures, IEEE Transactions on Power Delivery, vol. 23, No. 1, Jan. 2008, pp. 508-509.
S. Toyama et al., Highly Sensitive Detection Method of Dibenzyl Disulfide and the Elucidation of the Mechanism of Copper Sulfide Generation in Insulating Oil, IEEE Transactions on Dielectrics and Electrical Insulation, vol. 16, No. 2, Apr. 2009, pp. 509-515.
T. Amimoto et al., Duration and Mechanism for Suppressive Effect of Triazole-based Passivators on Copper-sulfide Deposition on Insulating Paper, IEEE Transactions on Dielectrics and Electrical Insulation, vol. 16, No. 1, Feb. 2009, pp. 257-264.
Maria Agusta el.., Experimental Study of the Role Played by Dibenzyl Disulfide on Insulating Oil Corrosivity—Effect of Passivator Irgamet 39, IEEE Electrical Insulation Magazine, vol. 26, No. 4, Jul./Aug. 2010, pp. 27-31.
S. Toyama et al., Influence of Inhibitor and Oil Components on Copper Sulfide Deposition on Kraft Paper in Oil-immersed Insulation, IEEE Transactions on Dielectrics and Electrical Insulation, vol. 18, No. 6, Dec. 2011, pp. 1877-1885.
K. Mizuno et al., Identification of Compounds Leading to Copper Sulfide formation on Insulating Paper in Transformers and the Degradation of Suppressing Effect of 1,2,3-Benzotriazole and Irgamet 39 in Insulating Oil, presented at the $76^{th}$ Ann. Int. Doble Client Conf., Doble Engineering Company, Boston, MA, 2009.
Takashi Ito et al., Partial Translation of "Quantitative Evaluation on Effect of Additives to Insulating Oil Sulfur Corrosion", Technical Meeting on Insulating Oil Section, JPI, Jun. 6, 2008, pp. 14-19.
Lian et al., "Causess and Countermeasures for Sulfur Corrosion of Insulation Oil in Transformers", Fujian Electricity and Electrician, Dec. 2008, vol. 28, Issue 4, pp. 17-20.
Chen et al., "The Application of Metal Deactivators in Transformer Oil to Improve Its Jerformance", Acta Pet Rolei S Inica (Petroleum Processing Section), Apr. 2003, vol. 19, Issue 2, pp. 62-69.
Office Action (Grounds for Rejection) dated Oct. 27, 2015, issued by the Chinese Patent Office in corresponding Chinese Patent Application No. 201180074369.1, and an English translation of the Office Action. (12 pages).

* cited by examiner

Primary Examiner — Maureen Wallenhorst
(74) Attorney, Agent, or Firm — Buchanan Ingersoll & Rooney PC

(57) ABSTRACT

The present invention is a method for preventing copper sulfide generation in oil-filled electrical equipment having an inhibitor of copper sulfide generation in insulating oil, and the method is characterized in monitoring characteristics of the insulating oil and performing re-addition of the inhibitor at an appropriate moment in accordance with a result of the monitoring.

6 Claims, 1 Drawing Sheet

METHOD FOR SUPPRESSING COPPER SULFIDE GENERATION IN OIL-FILLED ELECTRICAL EQUIPMENT

TECHNICAL FIELD

The present invention relates to a method for suppressing copper sulfide generation in oil-filled electrical equipment. More in detail, the present invention relates to a method for suppressing generation of copper sulfide on coil insulating paper in oil-filled electrical equipment (for example, a transformer) provided with coil copper which has the coil insulating paper wound therearound and is arranged in insulating oil.

BACKGROUND ART

In oil-filled electrical equipment such as an oil-filled transformer, coil copper as a conducting medium has coil insulating paper wound therearound so that a structure for preventing occurrence of short-circuit between adjoined turns is provided.

Meanwhile, mineral oil used in the oil-filled transformer contains a sulfur constituent, and the sulfur constituent reacts with coil copper arranged in oil, so that conductive copper sulfide is generated. In the case where this copper sulfide is generated on a surface of insulating paper provided on the coil, a conduction path is formed from a point at which copper sulfide is deposited because copper sulfide is a conductive substance. Consequently, there has been known disadvantages such as occurrence of electric breakdown due to short-circuit of adjoining coil turns (for example, NPD 1 (CIGRE WG A2-32, "Copper sulphide in transformer insulation," Final Report Brochure 378, 2009)).

Moreover, it has been known that a causative substance causing generation of copper sulfide is dibenzyldisulfide (DBDS) which is a kind of a sulfur compound in oil (for example, NPD 2 (F. Scatiggio, V. Tumiatti, R. Maina, M. Tumiatti, M. Pompilli and R. Bartnikas, "Corrosive Sulfur in Insulating Oils: Its Detection and Correlated Power Apparatus Failures", IEEE Trans. Power Del., Vol. 23, pp. 508-509, 2008)).

It has been known that copper sulfide is generated on coil insulating paper by a process in which DBDS reacts with coil copper to generate a complex, a process in which the complex is diffused in oil to adhere to coil insulating paper, and a process in which the adhered complex is dissolved to become copper sulfide (for example, NPD3 (S. Toyama, J. Tanimura, N. Yamada, E. Nagao and T. Amimoto, "Highly Sensitive Detection Method of Dibenzyl Disulfide and the Elucidation of the Mechanism of Copper Sulfide Generation in Insulating Oil", IEEE Transactions on Dielectrics and Electrical Insulation, Vol. 16, No. 2, pp. 509-515, 2009.)).

There has been a known method for suppressing copper sulfide generation by suppressing the reaction between DBDS and coil copper in accordance with the generation mechanism described above, and a method of adding an inhibitor to electric insulating oil is widely used. As an inhibitor of copper sulfide generation, 1,2,3-benzotriazole (BTA) or Irgamet39 is used (for example, NPD4 (T. Amimoto, E. Nagao, J. Tanimura, S. Toyama and N. Yamada, "Duration and Mechanism for Suppressive Effect of Triazole-based Passivators on Copper-sulfide Deposition on Insulating Paper", IEEE Transactions on Dielectrics and Electrical Insulation, Vol. 16, No. 1, pp. 257-264, 2009.)).

When an inhibitor of copper sulfide generation is added to oil, the inhibitor reacts with coil copper to form a coat on a surface of the coil copper (for example, PTD 1 (Japanese Patent Laying-Open No. 6-76635)). Since this formed coat blocks or suppresses reaction between DBDS and coil copper, copper sulfide generation can be suppressed (for example, NPD 4).

However, in the case where the inhibitor for suppressing copper sulfide generation is added to insulating oil, since the coat formed by the reaction between the inhibitor and coil copper is gradually peeled off due to oxidative degradation or thermal degradation, there is a possibility that the inhibitory effect of the coat is faded (for example, NPD 4). Meanwhile, although DBDS in insulating oil is also consumed by the thermal degradation, it is rarely consumed at the actual equipment operation temperature (for example, NPD 5 (Maria Augusta G. Martins and Ana R. Gomes, "Experimental Study of the Role Played by Dibenzyl Disulfide on Insulating Oil Corrosivity-Effect of Passivator Irgamet 39", IEEE Electrical Insulation Magazine, Vol. 26, No. 4 pp. 27-31, 2010.)). When the inhibitory effect of the coat is lost, the reaction between DBDS and coil copper recurs as long as DBDS is detected in insulating oil, thus copper sulfide is generated on insulating paper disadvantageously.

With respect to newly established equipment, when insulating oil not containing DBDS is used, a possibility of generation of copper sulfide is extremely low without adding the inhibitor. On the other hand, in the case where the inhibitor is applied with respect to existing equipment, there is a possibility that copper sulfide is generated immediately after the inhibitor is depleted. Therefore, there has been a problem of clarifying a criterion for determining a timing at which the inhibitory effect of the inhibitor is lost.

CITATION LIST

Patent Document

PTD 1: Japanese Patent Laying-Open No. 6-76635

Non Patent Document

NPD 1: CIGRE WG A2-32, "Copper sulphide in transformer insulation," Final Report Brochure 378, 2009

NPD 2: F. Scatiggio, V. Tumiatti, R. Maina, M. Tumiatti M. Pompilli and R. Bartnikas, "Corrosive Sulfur in Insulating Oils: Its Detection and Correlated Power Apparatus Failures", IEEE Trans. Power Del., Vol. 23, pp. 508-509, 2008

NPD 3: S. Toyama, J. Tanimura, N. Yamada, E. Nagao and T. Amimoto, "Highly Sensitive Detection Method of Dibenzyl Disulfide and the Elucidation of the Mechanism of Copper Sulfide Generation in Insulating Oil", IEEE Transactions on Dielectrics and Electrical Insulation, Vol. 16, No. 2, pp. 509-515, 2009.

NPD 4: T. Amimoto, E. Nagao, J. Tanimura, S. Toyama and N. Yamada, "Duration and Mechanism for Suppressive Effect of Triazole-based Passivators on Copper-sulfide Deposition on Insulating Paper", IEEE Transactions on Dielectrics and Electrical Insulation, Vol. 16, No. 1, pp. 257-264, 2009

NPD 5: Maria Augusta G. Martins and Ana R. Gomes, "Experimental Study of the Role Played by Dibenzyl Disulfide on Insulating Oil Corrosivity-Effect of Passivator Irgamet 39", IEEE Electrical Insulation Magazine, Vol. 26, No. 4 pp. 27-31, 2010

NPD 6: S. Toyama, K. Mizuno, F. Kato, E. Nagao, T. Amimoto, and N. Hosokawa, "Influence of Inhibitor and Oil Components on Copper Sulfide Deposition on Kraft Paper in Oil-immersed Insulation", to be published IEEE Transactions on Dielectrics and Electrical Insulation, Vol. 18, No. 6, pp. 1877-1885, 2011

NPD 7: K. Mizuno, S. Toyama, H. Kawarai, J. Tanimura, Y. Fujita, F. Kato, T. Amimoto, N. Hosokawa, and E. Nagao, "Identification of compounds leading to copper sulfide formation on insulating paper in transformers and the degradation of suppressing effect of 1,2,3-benzotriazole and Irgamet 39 in insulating oil", presented at the 76 th Ann. Int. Doble Client Conf., Doble Engineering Company, Boston, Mass., 2009

SUMMARY OF INVENTION

Technical Problem

The present invention was achieved to solve the problem described above, and its object is to provide a method for suppressing copper sulfide generation. The method is capable of preventing recurrence of copper sulfide generation in oil-filled electrical equipment by adding an inhibitor for suppressing copper sulfide generation to insulating oil and thereafter monitoring continuity of an inhibitory effect.

Solution to Problem

The inventors found out that recurrence of copper sulfide generation can be prevented by adding an inhibitor to insulating oil in oil-filled electrical equipment, monitoring characteristics of the insulating oil, and controlling a re-addition timing of the inhibitor, and came to the present invention.

In other words, the present invention is a method for suppressing copper sulfide generation in oil-filled electrical equipment having an inhibitor of copper sulfide generation in insulating oil, and the method includes:

monitoring characteristics of said insulating oil and performing re-addition of said inhibitor at an appropriate timing in accordance with a result of said monitoring.

Preferably, said insulating oil contains a causative substance causing copper sulfide generation or exhibits corrosiveness in an IEC62535 sulfidation corrosion test. Preferably, said causative substance is dibenzyldisulfide.

Preferably, an amount of copper in said insulating oil is analyzed during said monitoring, and said inhibitor is re-added at a moment at which a predetermined amount of copper is detected. Preferably, said moment at which a predetermined amount of copper is detected is a moment at which copper having a concentration of 0.1 ppm or greater in said insulating oil is detected.

Preferably, an amount of copper in said insulating oil is analyzed during said monitoring, and said inhibitor is re-added at a moment at which a tendency of fluctuation in a copper amount is changed.

Preferably, an amount of said inhibitor in said insulating oil is analyzed during said monitoring, and said inhibitor is re-added at a moment prior to depletion of said inhibitor. Preferably, the moment prior to depletion of said inhibitor is a moment at which a concentration of said inhibitor in said insulating oil is lowered to a predetermined threshold value or less.

Preferably, said insulating oil contains an oxidative degradation preventing agent.

Advantageous Effects of Invention

According to the present invention, an amount of copper and an amount of an inhibitor for suppressing copper sulfide generation in insulating oil are monitored, so that a re-addition timing of an inhibitor can be controlled in an optimal way, thus recurrence of copper sulfide generation can be prevented.

DESCRIPTION OF EMBODIMENTS

Figure 1:
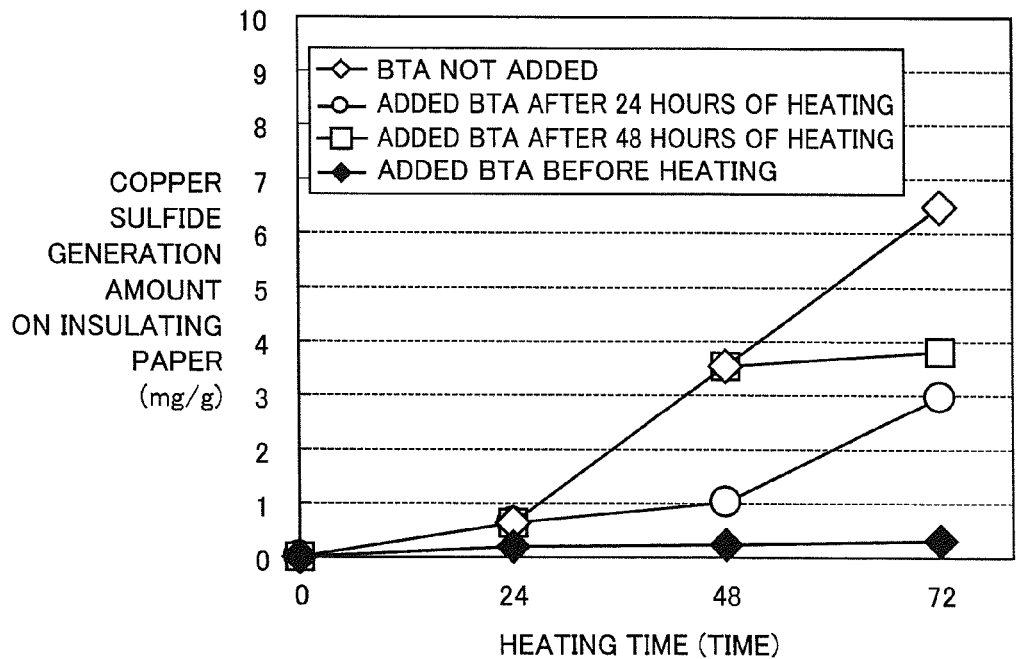
FIG. 1 is a graph representing a copper sulfide generation amount on insulating paper in a heating test of Test Example 1.

The present invention relates to a method for suppressing copper sulfide generation in oil-filled electrical equipment having an inhibitor of copper sulfide generation added to insulating oil. Herein, "having an inhibitor of copper sulfide generation added to insulating oil" includes not only the case where an inhibitor is added to insulating oil prior to beginning of use but also the case where the inhibitor is added to the insulating oil during the use. The present invention is characterized in performing monitoring on characteristics of insulating oil and performing re-addition of the inhibitor at an appropriate moment in accordance with a result of the monitoring.

The method for suppressing copper sulfide generation according to the present invention is preferably used in the case where the insulating oil contains a causative substance causing copper sulfide generation or exhibits corrosiveness in an IEC62535 sulfidation corrosion test. Typically, the causative substance is dibenzyldisulfide (DBDS).

The oil-filled electrical equipment is electrical equipment containing oil such as electric insulating oil, and includes a transformer having electric insulating oil enclosed therein. Open type oil-filled electrical equipment is oil-filled electrical equipment which is not sealed. Sealed type oil-filled electrical equipment is oil-filled electrical equipment which is sealed. The oil-filled electrical equipment is preferably a transformer.

Insulating oil used for open type oil-filled electrical equipment typically contains an oxidative degradation preventing agent. The oxidative degradation preventing agent includes, for example, di-t-butyl-p-cresol and di-t-butyl phenol. It is known that the di-t-butyl-p-cresol which is an oxidative degradation preventing agent is an accelerating factor of copper sulfide generation (for example, NPD 6 (S. Toyama, K. Mizuno, F. Kato, E. Nagao, T. Amimoto, and N. Hosokawa, "Influence of Inhibitor and Oil Components on Copper Sulfide Deposition on Kraft Paper in Oil-immersed Insulation", to be published IEEE Transactions on Dielectrics and Electrical Insulation, Vol. 18, No. 6, pp. 1877-1885, 2011)). As described above, since copper sulfide is particularly readily generated in oil-filled electrical equipment having an oxidative degradation preventing agent contained in insulating oil, the method for suppressing copper sulfide generation according to the present invention is preferably used.

Preferably, the inhibitor of copper sulfide generation is a benzotriazole compound. The benzotriazole compound includes, for example, 1,2,3-benzotriazole (BTA) and Irgamet (registered trademark) 39 [N,N-bis(2-ethylhexyl)-(4 or 5)-methyl-1H-benzotriazole-1-methylamine: manufactured by BASF Japan Ltd.].

Preferably, during "monitoring characteristics of insulating oil", an amount of copper or inhibitor in the insulating oil is analyzed. The amount of copper or inhibitor in the insulating oil can be detected by means of an existing technology.

For example, if measuring equipment such as an atomic absorption photometer or an HPLC (high performance liquid chromatography) is used, the amount can be determined to the extent of 0.1 ppmw.

First Embodiment

In the present embodiment, the amount of copper in insulating oil is analyzed during "monitoring characteristics of insulating oil", and the inhibitor is re-added at a moment at which a predetermined amount of copper is detected. The "moment at which a predetermined amount of copper is detected" is, for example, a moment at which copper having a concentration of 0.1 ppm or greater in insulating oil is detected.

Second Embodiment

In the present embodiment, the amount of copper in insulating oil is analyzed during "monitoring characteristics of insulating oil", and the inhibitor is re-added at a moment at which a tendency of fluctuation in a copper amount is changed (a moment of beginning to increase from a flat state, or a moment of ending a tendency of reduction and turning into a tendency of remaining flat or increasing).

Third Embodiment

In the present embodiment, the amount of inhibitor in insulating oil is analyzed during "monitoring characteristics of insulating oil", and the inhibitor is re-added at a moment prior to depletion of the inhibitor. The "moment prior to depletion of the inhibitor" is, for example, a moment at which a concentration of the inhibitor in the insulating oil is lowered to a predetermined threshold value or less. Preferably, the threshold value at this stage is 5 to 10 ppm.

As described above, the amount of copper or inhibitor for suppressing copper sulfide generation in insulating oil is monitored, so that the re-addition timing of the inhibitor can be optimized, thus recurrence of copper sulfide generation in oil-filled electrical equipment can be prevented.

EXAMPLE

Test Example 1

A copper sulfide generation test utilizing a IEC62535 sulfidation corrosion test was performed. A component analysis was also performed on insulating oil with changes in timings of adding the inhibitor of copper sulfide generation.

Firstly, to simulate coil copper insulated with coil insulating paper in a transformer, coil copper having one layer of coil insulating paper wound therearound was accommodated in a test container (a vial manufactured by Agilent Technologies). The insulating oil was poured into this test container, and a heating test (IEC62535 sulfidation corrosion test) was performed with use of a hot air circulation type drying furnace. As the insulating oil, the insulating oil having DBDS and an oxidative degradation preventing agent (di-t-butyl-p-cresol) dissolved therein (DBDS and di-t-butyl-p-cresol are dissolved in mineral oil (new oil) used for an oil-filled transformer) was used.

As conditions readily generating copper sulfide on the insulating paper, a heating temperature was set to be 150° C., and a heating time period was set to be 72 hours. As the inhibitor of copper sulfide generation, BTA (C.V.I. (registered trademark): manufactured by Chelest Corporation) was used. This inhibitor was added to the insulating oil before heating, 24 hours after heating, and 48 hours after heating. It should be noted that an air atmosphere is present above an oil level of insulating oil accommodated in the test container, and an inflow of air from outside is blocked during the test. Until an elapse of 72 hours from starting the heating test, the amount of copper sulfide generation on the insulating paper, the copper amount in the insulating oil, and the concentration of the inhibitor (BTA) were analyzed at intervals of 24 hours with use of the atomic absorption photometer or HPLC (high performance liquid chromatography).

Figure 2:
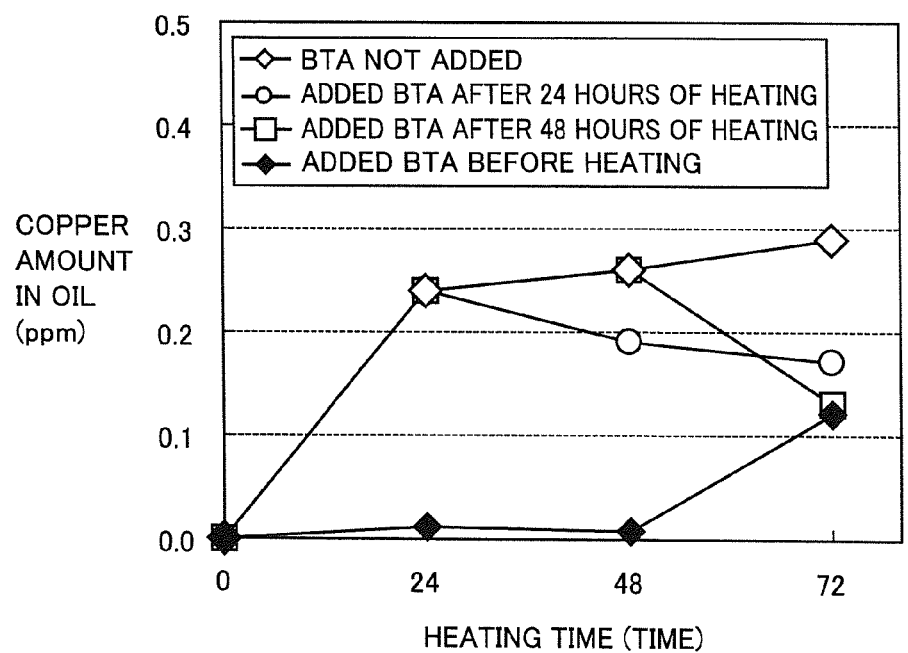
FIG. 2 is a graph representing a copper amount in insulating oil in the heating test of Test Example 1.

An analysis result of the amount of copper sulfide generation on the insulating paper is shown in FIG. 1, and an analysis result of the copper amount is shown in FIG. 2. Although the analysis result of the BTA concentration is not illustrated in the drawings, regardless of the addition timing of the inhibitor (BTA), the BTA concentration was lowered to the analytical sensitivity or less at the moment of an elapse of 24 hours from adding the BTA.

As shown in FIG. 1, with the oil having no BTA added, some copper sulfide was generated on the insulating paper from 24 hours of heating, and the copper sulfide was subsequently generated at a constant rate. On the other hand, with the oil having the BTA added before heating, the copper sulfide generation amount on the insulating paper was very small. With the oil having the BTA added after heating for 24 hours or 48 hours, the copper sulfide generation amount on the insulating paper was smaller as compared to the oil having no BTA added. With the oil having the BTA added after heating for 24 hours, the copper sulfide generation amount slightly increased in 0 to 24 hours, and further rapidly increased in 24 to 48 hours.

As shown in FIG. 2, with the oil having no BTA added, a copper amount in the oil was detected after heating for 24 hours, and subsequently shifted in a flat state. Moreover, with the oil having the BTA added before heating, the amount of copper in oil was small until 48 hours of heating, but copper of 0.1 ppm or greater was detected at the moment of 72 hours of heating. In this stage, a coat generated by reaction between the inhibitor and the coil copper started to be peeled off due to oxidative degradation or thermal degradation, thus it was considered that the reaction between the DBDS and the coil copper was performed. From this result, it was determined that the inhibitory effect was lost at the moment at which the copper amount of 0.1 ppm or greater in the oil was detected or at the moment at which the copper amount in the oil started to increase (the moment at which a tendency of fluctuation in the copper amount is changed), thus it was considered that applying the inhibitor was effective.

Meanwhile, few or no copper sulfide was generated on the insulating paper at the moment of 72 hours of heating. This is attributed to the fact that it took a long time for copper sulfide to be formed on the surface of insulating paper since the copper sulfide was formed, subsequent to the reaction performed between the DBDS and the coil copper, on the insulating paper through diffusion of a reactive product in oil, adhesion to the surface of insulating paper, and thermal decomposition of the product (for example, NPD 3).

It is known that the concentration of the inhibitor is reduced due to thermal degradation or oxidative degradation after the inhibitor is added to oil. Thus, it is necessary to re-add the inhibitor before depletion of the inhibitor. Moreover, since it is difficult to monitor the concentration of the inhibitor on a steady basis, it is necessary to find the concentration of the inhibitor by analyzing the oil periodically extracted from the transformer. On the other hand, for the purpose of reducing the frequency of the operation for re-adding the inhibitor to the transformer, it is necessary to reduce the frequency of adding the inhibitor to be as small as possible. Thus, it is preferable to re-add the inhibitor when the concentration of the inhibitor reaches a threshold value set in advance. To perform re-addition before complete depletion of the inhibitor, and reduce the frequency of re-addition of the inhibitor, it is preferable to set the threshold value of the concentration of the inhibitor to be 5 to 10 ppm.

In the present heating test with the heating temperature of 150° C., the inhibitor (BTA) was depleted in one day. Taking in consideration that lowering the temperature of the insulating oil by 10° C. causes the reduction rate of the inhibitor to be lowered to about ½ (for example, NPD 7 (K. Mizuno, S. Toyama, H. Kawarai, J. Tanimura, Y. Fujita, F. Kato, T. Amimoto, N. Hosokawa, and E. Nagao, "Identification of compounds leading to copper sulfide formation on insulating paper in transformers and the degradation of suppressing effect of 1,2,3-benzotriazole and Irgamet 39 in insulating oil", presented at the 76th Ann. Int. Doble Client Conf., Doble Engineering Company, Boston, Mass., 2009.)), the inhibitor is almost depleted in 128 days in the case where the heating temperature is set to be 70° C. which is close to an average operation temperature of the transformer. From this, taking in consideration that the actually operating transformer has temperature distribution, and the operation load may be fluctuated, and also taking in consideration the analysis accuracy for the concentration of the inhibitor, it is considered preferable to analyze the concentration of the inhibitor at the intervals of three months after adding the inhibitor.

With the oil having the BTA added after 24 hours of heating or after 48 hours of heating, the amount of copper in oil is reduced after addition. During the period in which the BTA is present in the oil, the amount of copper in the oil is reduced. Since the reaction between the DBDS and the coil copper recurs when the BTA is depleted, the amount of copper in oil is shifted while consumption by the copper sulfide generation and the supply by the reaction between the coil the DBDS and the coil copper are balanced after the depletion of the BTA.

From FIGS. 1 and 2, and the BTA analysis result, it became apparent that the timing of adding the inhibitor significantly affect the continuity of the inhibitory effect of the copper sulfide generation. It was found that the continuity of the inhibitory effect in the oil having the inhibitor added after heating is shorter than that of the case with the oil having the inhibitor added before heating.

Also in the case where the similar test was separately performed with use of Irgamet (registered trademark) 39 (manufactured by BASF Japan Ltd.) as an inhibitor, the inhibitory effect for copper sulfide generation similar to the case with the BTA was obtained. It is predicted that the result which is the same as the case with di-t-butyl-p-cresol can be obtained also in the case of using di-t-butyl phenol as an oxidative degradation preventing agent.

It is to be understood that the embodiments disclosed herein are only by way of example, and not to be taken by way of limitation. The scope of the present invention is not limited by the description, but rather by the terms of appended claims, and is intended to include any modifications within the scope and meaning equivalent to the terms of claims.

The invention claimed is:

1. A method for suppressing copper sulfide generation in oil-filled electrical equipment having an inhibitor of copper sulfide generation in insulating oil, the method comprising:
monitoring an amount of copper in said insulating oil and performing re-addition of said inhibitor in response to detecting copper having a concentration of 0.1 ppm or greater in said insulating oil, or in response to detecting that said amount of copper in said insulating oil begins to increase from a flat state, or ends a tendency of reduction and turns into a tendency of remaining flat or increasing, in accordance with a result of said monitoring.

2. The method for suppressing copper sulfide generation according to claim 1, wherein said insulating oil contains a causative substance causing copper sulfide generation or exhibits corrosiveness in an IEC62535 sulfidation corrosion test.

3. The method for suppressing copper sulfide generation according to claim 2, wherein said causative substance is dibenzyldisulfide.

4. The method for suppressing copper sulfide generation according to claim 1, wherein an amount of said inhibitor in said insulating oil is monitored during said monitoring, and said inhibitor is re-added prior to depletion of said inhibitor.

5. The method for suppressing copper sulfide generation according to claim 4, wherein said inhibitor is added in response to detecting a concentration of said inhibitor in said insulating oil is a predetermined threshold value or less.

6. The method for suppressing copper sulfide generation according to claim 1, wherein said insulating oil contains an oxidative degradation preventing agent.

* * * * *